(12) United States Patent
Chida et al.

(10) Patent No.: US 11,090,471 B2
(45) Date of Patent: Aug. 17, 2021

(54) MEDICAL DEVICE FOR TREATING LYMPHEDEMA

(71) Applicant: TERUMO KABUSHIKI KAISHA, Tokyo (JP)

(72) Inventors: Takahiro Chida, Kanagawa (JP); Manabu Miura, Kanagawa (JP); Souta Kimura, Kanagawa (JP); Saki Yokoyama, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 601 days.

(21) Appl. No.: 15/901,488

(22) Filed: Feb. 21, 2018

(65) Prior Publication Data

US 2018/0236212 A1 Aug. 23, 2018

(30) Foreign Application Priority Data

Feb. 23, 2017 (JP) .............................. JP2017-032648

(51) Int. Cl.
*A61M 27/00* (2006.01)
*A61B 17/34* (2006.01)
*A61M 5/00* (2006.01)
*A61M 25/06* (2006.01)
(Continued)

(52) U.S. Cl.
CPC ......... *A61M 27/00* (2013.01); *A61B 17/3415* (2013.01); *A61M 5/00* (2013.01); *A61M 25/065* (2013.01); *A61M 27/002* (2013.01); *A61B 5/0071* (2013.01); *A61B 5/489* (2013.01); *A61M 1/0066* (2013.01); *A61M 2027/004* (2013.01); (Continued)

(58) Field of Classification Search
CPC .......... A61B 17/11; A61B 2017/00898; A61B 2017/00566; A61B 17/3468; A61B 17/3478; A61B 2017/1139; A61B 2017/1135; A61B 2017/1132;
(Continued)

(56) References Cited

U.S. PATENT DOCUMENTS 5,925,054 A * 7/1999 Taylor .................... A61B 17/11
606/153
10,220,134 B2 * 3/2019 Kunis ................ A61B 17/3478
(Continued)

FOREIGN PATENT DOCUMENTS

JP 2009-544339 A 12/2009
JP 2016-067383 A 5/2016
(Continued)

OTHER PUBLICATIONS

Office Action (Notice of Reasons for Refusal) dated Jun. 23, 2020, by the Japanese Patent Office in corresponding Japanese Patent Application No. 2017-032648 and an English Translation of the Office Action. (6 pages).

*Primary Examiner* — Nicholas J Weiss
*Assistant Examiner* — Alessandro R Del Priore
(74) *Attorney, Agent, or Firm* — Buchanan Ingersoll & Rooney PC

(57) ABSTRACT

A medical device is disclosed, which is capable of treating lymphedema and reducing a reoccurrence rate after treatment. The medical device includes a tube member that includes a first end portion connected to a first body lumen L and a second end portion connected to a second body lumen P and a pressure-feeding unit that pressure-feeds a body fluid in the first body lumen to the second body lumen.

18 Claims, 11 Drawing Sheets

(51) Int. Cl.
  *A61M 1/00* (2006.01)
  *A61B 5/00* (2006.01)
(52) U.S. Cl.
  CPC ............... *A61M 2202/0021* (2013.01); *A61M 2202/0405* (2013.01); *A61M 2205/10* (2013.01)
(58) Field of Classification Search
  CPC ..... A61B 2017/1107; A61B 17/06066; A61M 2202/0405; A61M 27/002; A61M 39/0247
  See application file for complete search history.

(56) References Cited

U.S. PATENT DOCUMENTS

| | | | | |
|---|---|---|---|---|
| 2002/0065524 | A1* | 5/2002 | Miller | A61B 17/068 606/139 |
| 2002/0173809 | A1* | 11/2002 | Fleischman | A61B 17/11 606/153 |
| 2007/0282380 | A1 | 12/2007 | Brooke et al. | |
| 2008/0009719 | A1 | 1/2008 | Shuros et al. | |
| 2010/0121358 | A1* | 5/2010 | Blatter | A61B 17/11 606/155 |
| 2013/0150770 | A1* | 6/2013 | Horvath | A61F 2/82 604/8 |
| 2015/0209509 | A1* | 7/2015 | O'Cearbhaill | A61M 5/1582 604/506 |
| 2016/0278780 | A1 | 9/2016 | Ishii et al. | |
| 2017/0197066 | A1* | 7/2017 | Itkin | A61M 39/24 |

FOREIGN PATENT DOCUMENTS

| | | |
|---|---|---|
| JP | 2016-185254 A | 10/2016 |
| WO | 2015/200797 A2 | 12/2015 |

* cited by examiner

FIG. 10A
FIG. 10B
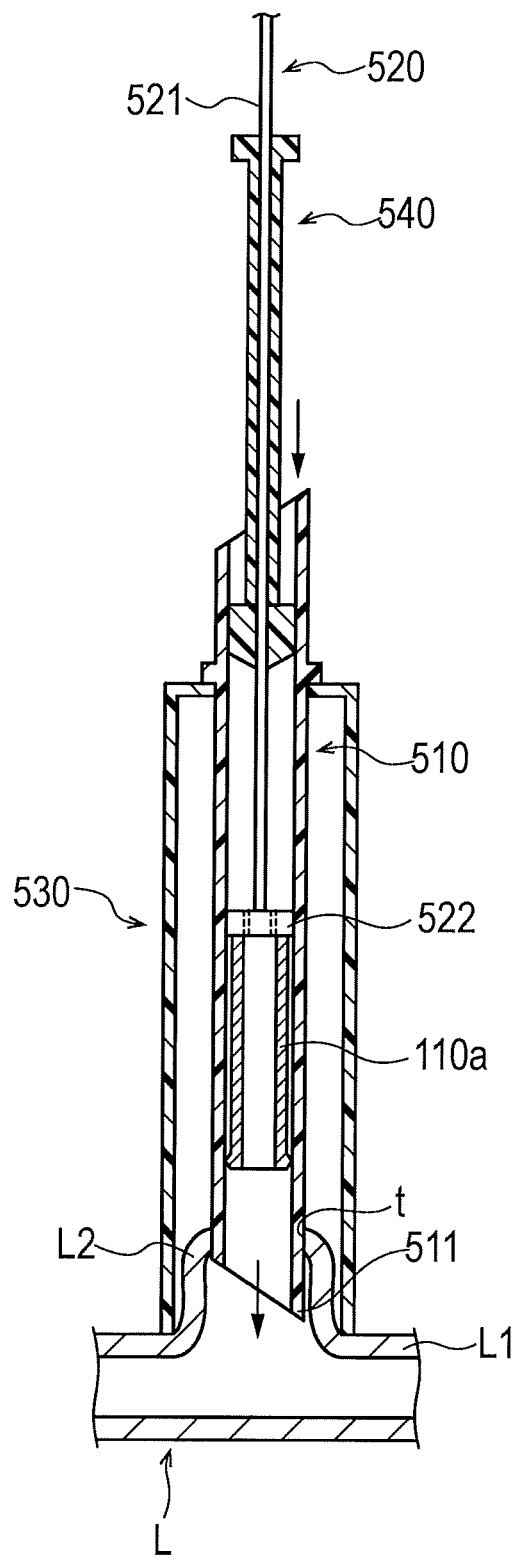
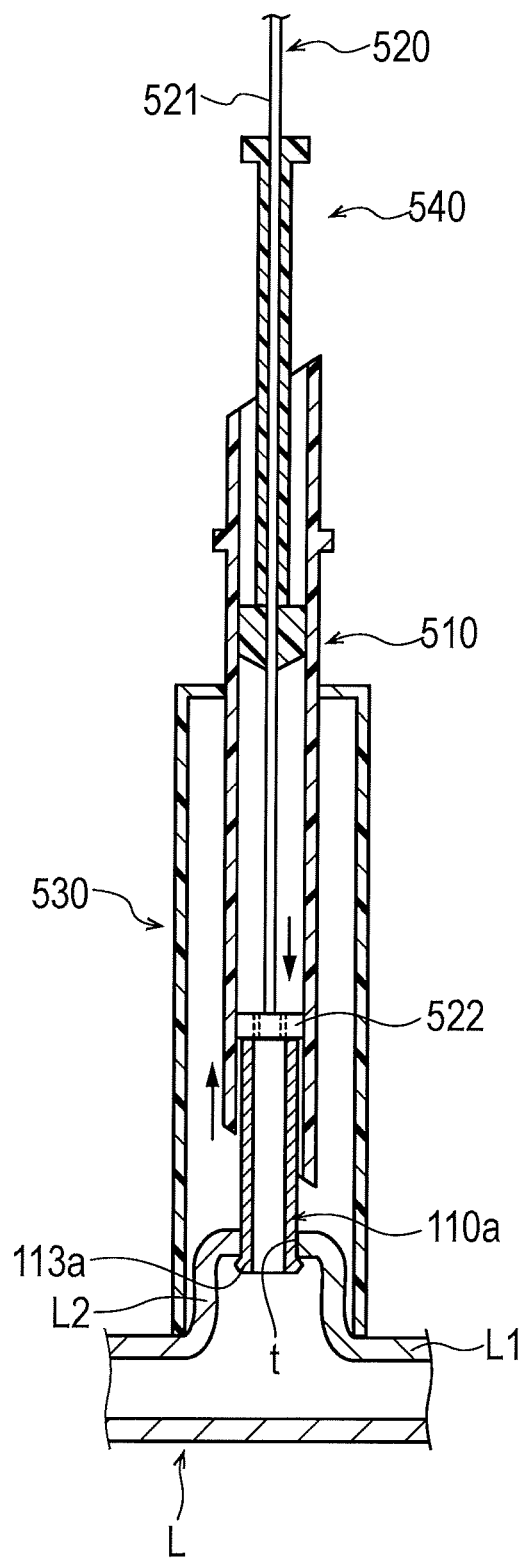

MEDICAL DEVICE FOR TREATING LYMPHEDEMA

CROSS-REFERENCES TO RELATED APPLICATIONS

This application claims priority to Japanese Application No. 2017-032648 filed on Feb. 23, 2017, the entire content of which is incorporated herein by reference.

TECHNICAL FIELD

The present disclosure relates to a medical device used for treating lymphedema.

BACKGROUND DISCUSSION

Lymphedema is a disease that develops as a lymph fluid that flows in lymphatic vessels existing in a living body stagnates and locally stays outside the lymphatic vessels.

As a lymphedema treatment method, for example, a compression method of relieving symptoms by attaching a medical device that applies a compression force to each part of a body in which swelling has occurred due to lymphedema, an administration method of administering a drug having a therapeutic effect for lymphedema (see JP-T-2009-544339 (the term "JP-T" as used herein means a published Japanese translation of a PCT patent application)), lymphaticovenular anastomosis (LVA) of performing a treatment by anastomosis (bypass) between a vein and a lymphatic vessel through a surgical treatment so that a lymph fluid flows into the vein, and the like are known. Among these treatment methods, the lymphaticovenular anastomosis has been gaining attention recently due to the high treatment effect in the early stage of developing lymphedema.

However, in the above-described lymphaticovenular anastomosis, since the vein or the lymphatic vessel used in the lymphaticovenular anastomosis is clogged by impurities and thrombus or the flow of the lymph fluid stagnates due to a decrease in lymphatic vessel pressure if time passes after surgery, there is a possibility that lymphedema may reoccur. For this reason, the rate of occlusion of the lymphatic vessel after the lymphaticovenular anastomosis is as high as 60% within two years after the surgery. When the lymphedema reoccurs, there is a need to find a lymphatic vessel different from the lymphatic vessel used in the lymphaticovenular anastomosis and to again perform the lymphaticovenular anastomosis.

SUMMARY

A medical device is disclosed, which is capable of treating lymphedema and reducing a reoccurrence rate after treatment.

In accordance with an exemplary embodiment, a medical device is disclosed, which includes: a tube member that includes a first end portion connected to a first body lumen and a second end portion connected to a second body lumen; and a pressure-feeding unit that pressure-feeds a body fluid in the first body lumen to the second body lumen.

According to the medical device of the invention, when the first body lumen (a lymphatic vessel) and the second body lumen (a vein) are connected to each other through the tube member and the body fluid (a lymph fluid) in the first body lumen is pressure-fed to the second body lumen by the pressure-feeding unit, the body fluid can be forcibly delivered. Further, when the body fluid in the first body lumen is periodically pressure-fed to the second body lumen by the pressure-feeding unit, substances causing clogging can forcibly flow. As a result, it is possible to treat lymphedema and to reduce a reoccurrence rate after the treatment of the lymphedema.

A medical device is disclosed comprising: a tube member having a first end portion is configured to be indwelled into a lymphatic vessel and a second end portion configured to be indwelled into a vein; a pressure-feeding unit that pressure-feeds a body fluid in the lymphatic vessel to the vein; a first catheter unit that connects the lymphatic vessel to the first end portion of the tube member while being indwelled in the lymphatic vessel; a second catheter unit that connects the vein to the second end portion of the tube member while being indwelled in the vein; a puncture member having a lumen capable of accommodating the first catheter unit and includes a needle tip punctured into the lymphatic vessel; a plunger which operates a movement of the first catheter unit accommodated in the puncture member; an outer cylinder, which is disposed to cover an outer periphery of the puncture member; and a negative pressure generating unit, which generates a negative pressure for deforming a vessel wall of the lymphatic vessel toward the puncture member when puncturing the lymphatic vessel with the puncture member.

BRIEF DESCRIPTION OF THE DRAWINGS

FIGS. 10A and 10B are cross-sectional views schematically illustrating procedure examples using the medical instrument according to the second embodiment.

DETAILED DESCRIPTION

Hereinafter, embodiments of the invention will be described with reference to the drawings. In addition, the dimensional ratios of the drawings may be exaggerated for convenience of description and may differ from the actual ratios.

First Embodiment

Figure 1:
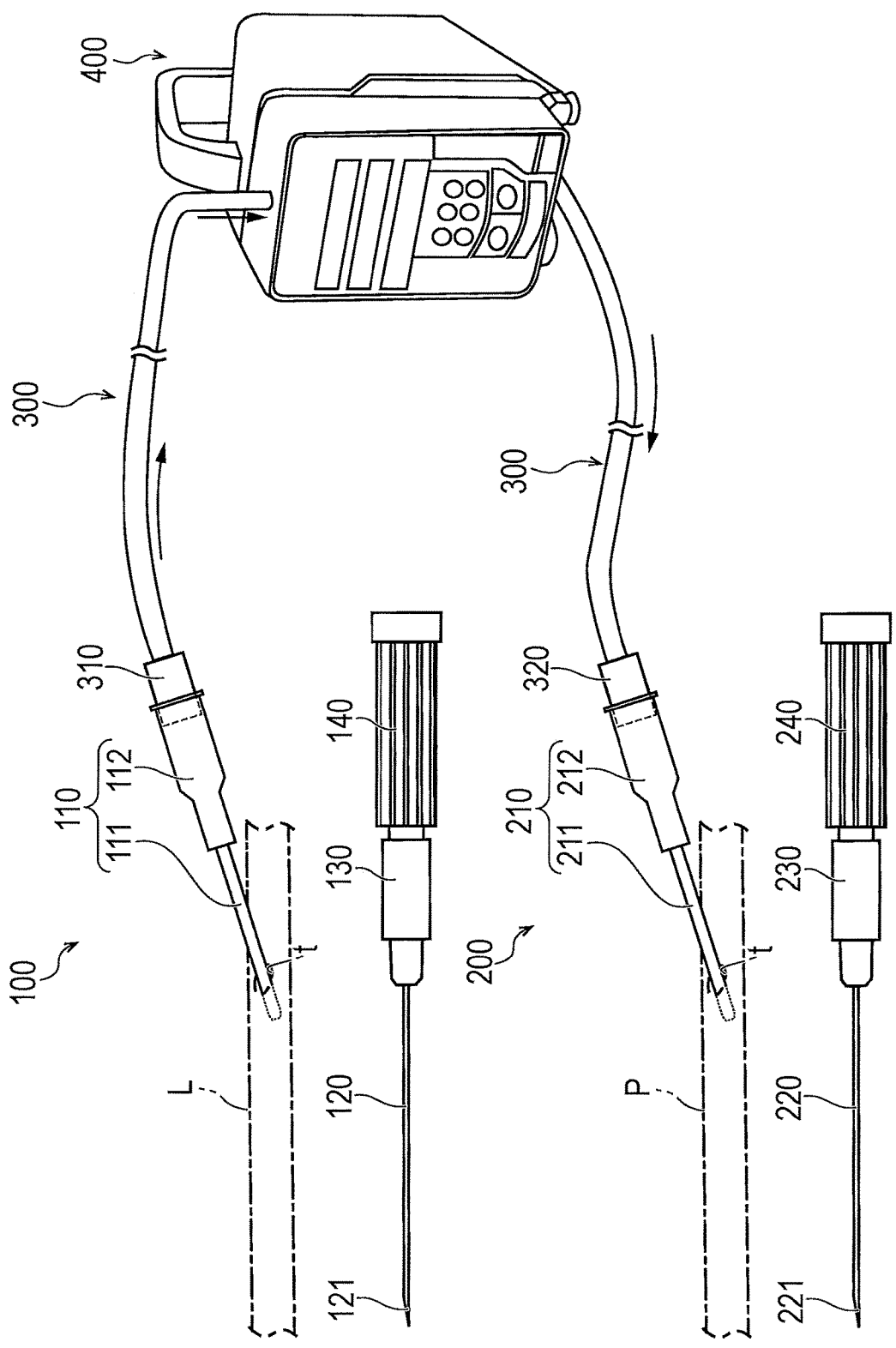
FIG. 1 is a schematic diagram illustrating an overall configuration of a medical device according to a first embodiment.
Figure 2:
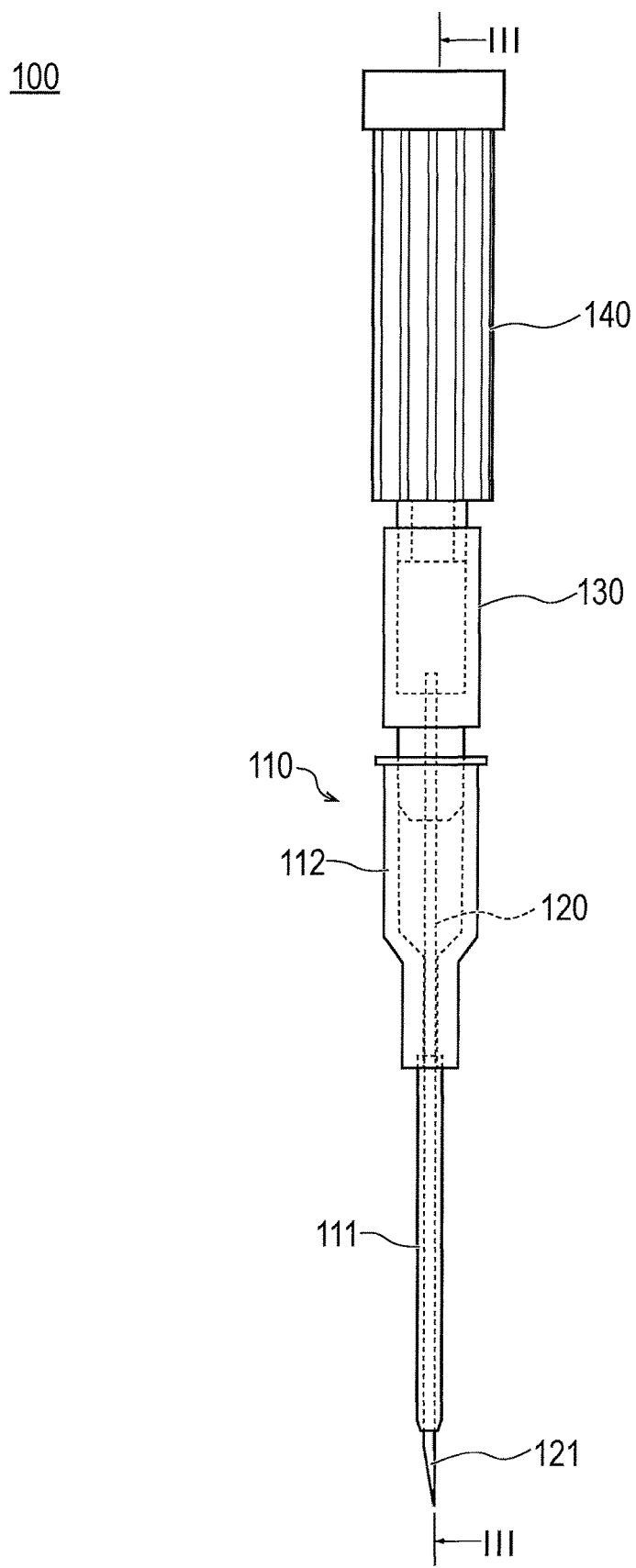
FIG. 2 is a side view of an indwelling needle according to the first embodiment.
Figure 3:
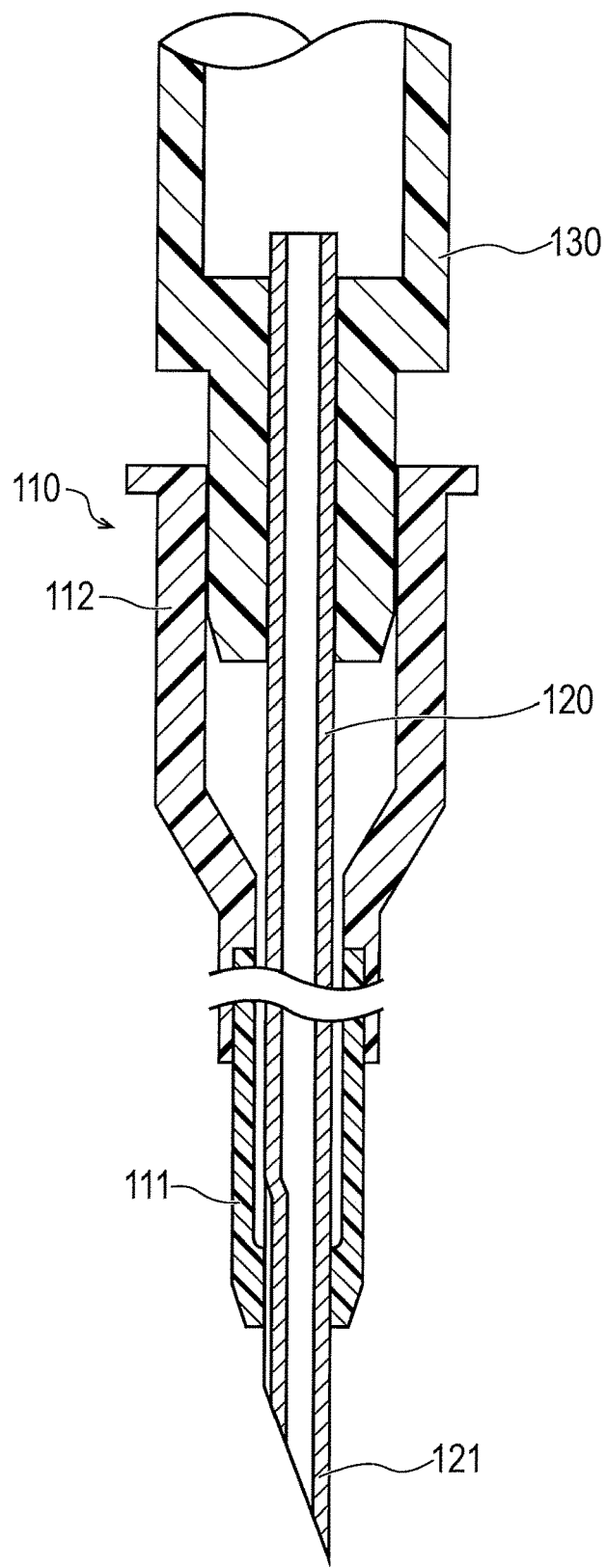
FIG. 3 is an enlarged cross-sectional view of the indwelling needle according to the first embodiment.

FIG. 1 is a schematic diagram illustrating an overall configuration of a medical device 10 according to a first embodiment, FIG. 2 is a side view of a first indwelling needle 100, and FIG. 3 is an enlarged cross-sectional view of the first indwelling needle 100 taken along a line III-III illustrated in FIG. 2.

The medical device 10 according to the embodiment is configured as a lymphedema treatment medical device capable of treating lymphedema and preventing reoccurrence thereof by causing a lymph fluid to forcibly flow from a lymphatic vessel L of a patient suffering from lymphedema toward a vein P.

As illustrated in FIG. 1, the medical device 10 generally includes a first indwelling needle 100 which includes a first catheter unit 110 indwelled in a lymphatic vessel L (corresponding to a first body lumen), a second indwelling needle 200 which includes a second catheter unit 210 punctured into a vein P (corresponding to a second body lumen) to be indwelled therein, a tube member 300 which connects the first catheter unit 110 and the second catheter unit 210 to each other, and a pump 400 (corresponding to a pressure-feeding unit) which pressure-feeds a lymph fluid (corresponding to a body fluid) in the lymphatic vessel L to the vein P through the tube member 300.

Indwelling Needles 100 and 200

The first indwelling needle 100 and the second indwelling needle 200 will be described. Further, in the specification, the first indwelling needle 100 and the second indwelling needle 200 will be generally referred to as an indwelling needle.

As illustrated in FIG. 1, the first indwelling needle 100 can include the first catheter unit 110, an inner needle 120 which includes a needle tip 121 puncturing the lymphatic vessel L while being disposed in an inner lumen of the first catheter unit 110 (see FIG. 2), an inner needle hub 130 which is attached to a proximal end side of the inner needle 120, and a grasping unit 140 which is connected to a proximal end side of the inner needle hub 130.

In addition, in the description of the first indwelling needle 100 and the second indwelling needle 200, a side (the lower side of FIG. 2) in which the inner needles 120 and 220 puncture the lymphatic vessel L and the vein P will be referred to as a distal side and a side (the upper side of FIG. 2) in which the grasping units 140 and 240 are disposed will be referred to as a proximal end side.

Figure 6A:
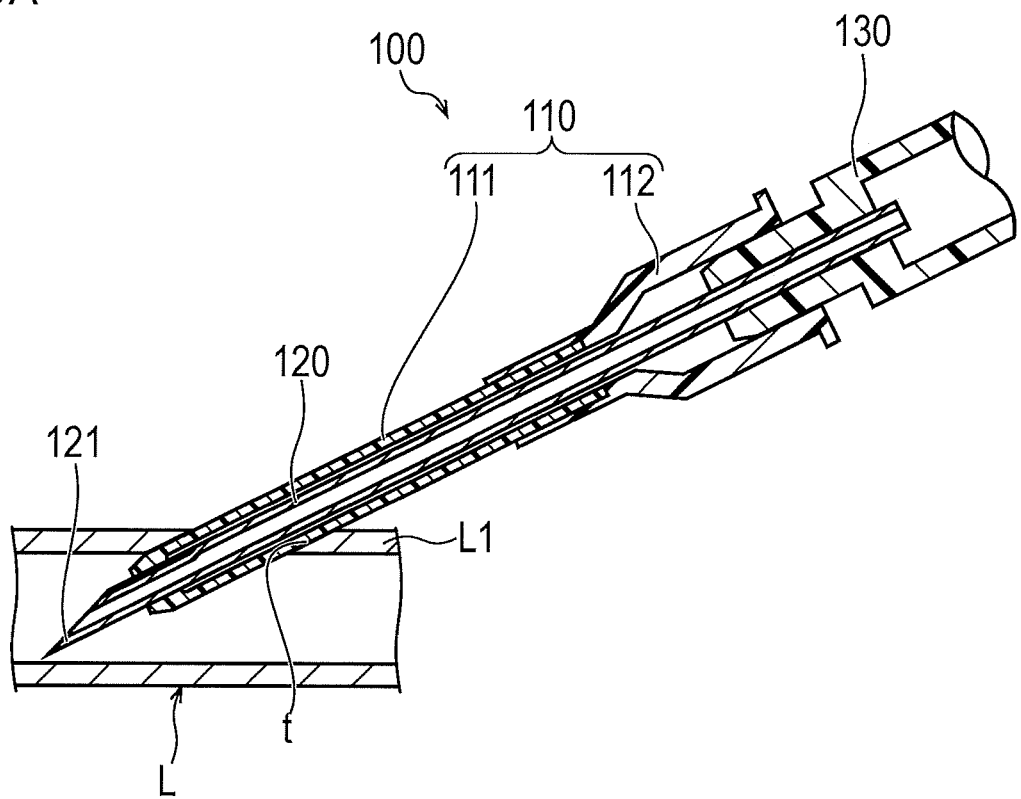
FIGS. 6A and 6B are cross-sectional views schematically illustrating procedure examples using the indwelling needle according to the first embodiment.
Figure 6B:
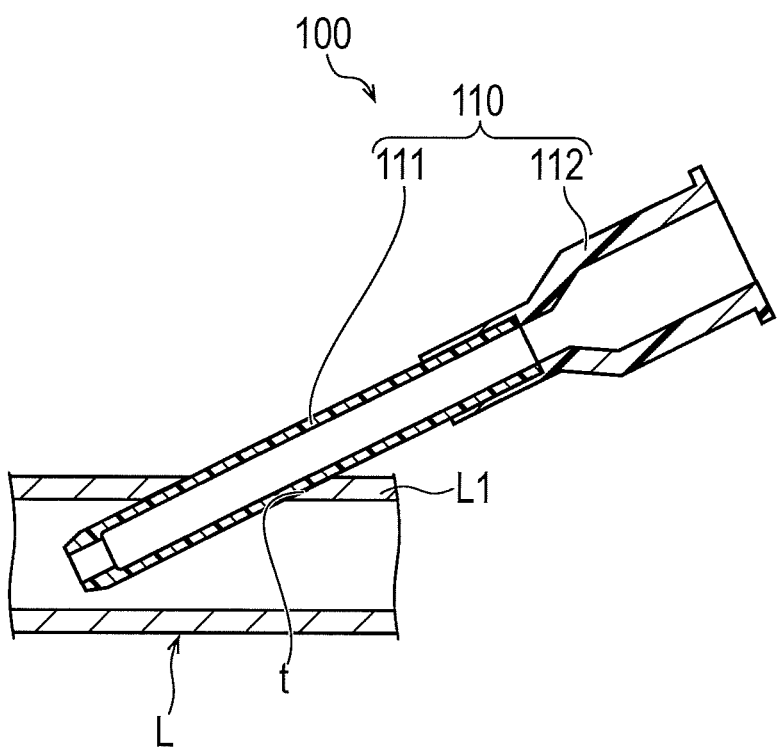

The first indwelling needle 100 has a configuration in which the first catheter unit 110 is separable from other constituting members (the inner needle 120, the inner needle hub 130 and the grasping unit 140). Accordingly, the first indwelling needle 100 can puncture the lymphatic vessel L in an assembled state as illustrated in FIG. 6A and can indwell only the first catheter unit 110 in the lymphatic vessel L as illustrated in FIG. 6B.

In accordance with an exemplary embodiment, the first catheter unit 110 can include a sheath 111 which has a lumen and is indwelled in the lymphatic vessel L and a catheter hub 112 which is attached to a proximal end side of the sheath 111.

In accordance with an exemplary embodiment, it is desirable that the sheath 111 has flexibility and be entirely or partially transparent. Since the sheath 111 is partially or entirely transparent, it is possible to visually recognize a state where a body fluid such as blood or lymph fluid flows into the sheath 111.

The catheter hub 112 has a configuration in which a first end portion 310 of the tube member 300 to be described later is connectable to the catheter hub 112. The catheter hub 112 can liquid-tightly connect the sheath 111 and the tube member 300 to each other while the first end portion 310 of the tube member 300 is connected to the catheter hub 112.

As illustrated in FIGS. 2 and 3, in a state where the inner needle 120 is inserted into an inner lumen of the sheath 111, the needle tip 121 of the distal end protrudes toward a distal end side in relation to the sheath 111. In this state, a distal end of the sheath 111 is disposed in the vicinity of a distal end of the inner needle 120. Accordingly, when the distal end of the inner needle 120 is inserted into the lymphatic vessel L, the sheath 111 is also inserted into the same lymphatic vessel L.

As illustrated in FIG. 1, the second indwelling needle 200 includes the second catheter unit 210, an inner needle 220 which includes a needle tip 221 capable of puncturing the vein P, an inner needle hub 230 which is attached to a proximal end side of the inner needle 220, and a grasping unit 240 which is connected to a proximal end side of the inner needle hub 230. In addition, since the second indwelling needle 200 have substantially the same configuration as the first indwelling needle 100, a part of the first indwelling needle 100 corresponding to FIGS. 2 and 3 is not illustrated.

The second catheter unit 210 can include a sheath 211 which includes a lumen and is indwelled in the vein P and a catheter hub 212 which is attached to a proximal end side of the sheath 211.

The catheter hub 212 has a configuration in which a second end portion 320 of the tube member 300 to be described later is connectable to the catheter hub 212. In a state where the catheter hub 212 is connected to a second end portion 320 of the tube member 300, the sheath 211 and the tube member 300 can be liquid-tightly connected to each other.

The material of the sheaths 111 and 211 is not particularly limited, but examples thereof include at least one or more resin selected from the group consisting of methacrylic resin such as polyolefin such as polyethylene, polypropylene, and ethylene-vinyl acetate copolymer, polyolefin elastomer, polyvinyl chloride, polyester, polyester elastomer, polyether nylon, polyamide, polyamide elastomer, polyurethane, polyurethane elastomer, polystyrene, polyacetal, polycarbonate, and polymethyl methacrylate, fluororesin such as polyvinyl alcohol, polysulfone, polyimide, polyether imide, polyether sulfone, polyether ether ketone, polybutadiene, and ethylene-tetrafluoroethylene, and silicone resin. In addition, one kind of the above-described resins may be used alone or two or more kinds thereof may be used in the form of a mixture. Further, a hydrophilic coating may be applied to the outer surfaces of the sheaths 111 and 211 in order to improve the slidability with respect to the inner walls of the lymphatic vessel L and the vein P.

In accordance with an exemplary embodiment, the outer diameters of the sheaths 111 and 211 can be appropriately selected in accordance with the outer diameter of the vein P or the lymphatic vessel L corresponding to a treatment target, but may be desirably formed to be, for example, 0.8 mm or less. When the outer diameters of the lymphatic vessel L and the vein P are, for example, about 1 mm, the outer diameter of the sheath 111 can be set to, for example, about 0.7 mm. Since the outer diameters of the sheaths 111 and 211 are set as described above, a less invasive procedure becomes possible. Further, in accordance with an exemplary embodiment, it is desirable that the inner diameters of the sheaths 111 and 211 be, for example, 0.35 mm or more. Since the inner diameters of the sheaths 111 and 211 are set as described above, it is possible to promptly treat lymphedema by securing the flow rate of lymph fluid to be delivered.

Tube Member 300

As illustrated in FIG. 1, the tube member 300 includes the first end portion 310 which is connected to the lymphatic vessel L through the first catheter unit 110 and the second end portion 320 which is connected to the vein P through the second catheter unit 210. In accordance with an exemplary embodiment, the pump 400 is disposed between the first end portion 310 and the second end portion 320 of the tube member 300.

An outer diameter of the tube member 300 is not particularly limited, but can be set to, for example, 0.8 mm or less.

Since the protein concentration of the lymph fluid flowing in the tube member 300 is very high, there is a possibility that the tube member 300 may be clogged when a large amount of protein is adsorbed onto the inner surface of the tube member 300. For this reason, it is desirable to form an adhesion preventing surface, which is coated with a coating for preventing the adhesion of protein or the like, on the inner surface of the tube member 300.

For example, the adhesion preventing surface may be formed by forming a surface having a hydrophilic coating, a fluorine-based coating, a silicon-based coating, or a fine unevenness structure, a surface having a combination of the coating and the unevenness structure, and a surface stably keeping silicone oil and fluorine oil not mixed with blood at an arbitrary position of the tube member 300.

Further, since there is a possibility that blood may contact the inner surface of the tube member 300, it is desirable to apply various coatings thereto. For example, it is possible to blend an antithrombogenic substance in the material constituting the tube member 300 or to coat the inner surface of the tube member 300 with an antithrombogenic substance. In particular, for example, since the second end portion 320 is highly likely to contact the blood in the vein P, it can be desirable to add an antithrombotic property to the inner surface of the second end portion 320 in order to prevent the adhesion of thrombus.

As the above-described antithrombogenic substance, it is possible to use heparin, a heparin-like substance, poly(2 methoxyethyl acrylate) (PMEA), polyethylene glycol (PEG), a betaine type zwitterionic polymer, or the like.

Pump 400

In accordance with an exemplary embodiment, the pump 400 can include a peristaltic pump mechanism which incorporates a part of the tube member 300, presses the outer peripheral surface of the tube member 300 by a plurality of fingers (not illustrated), and pressure-feeds the lymph fluid in the lymphatic vessel L to the vein P by peristalizing the tube member 300.

For example, the pump mechanism is configured so that the lymph fluid can be delivered at an appropriate flow rate by moving the fingers forward and backward at a predetermined cycle with respect to the tube member 300 in synchronization with the rotation of a cam shaft (not illustrated) having a plurality of eccentric cams. More specifically, when the pressing of the fingers disposed at the upstream side in the lymph fluid delivery direction is released so that the lymph fluid flows into the tube member 300 and the fingers are deformed to peristaltically move to sequentially press the tube member 300 in the lymph fluid delivery direction, the lymph fluid can be delivered. Since such a peristaltic pump mechanism is provided, the pump 400 can adjust the flow rate of the lymph fluid to be delivered.

Next, an example of use of the medical device 10 according to the embodiment will be described with reference to FIGS. 4 to 6.

Figure 4:
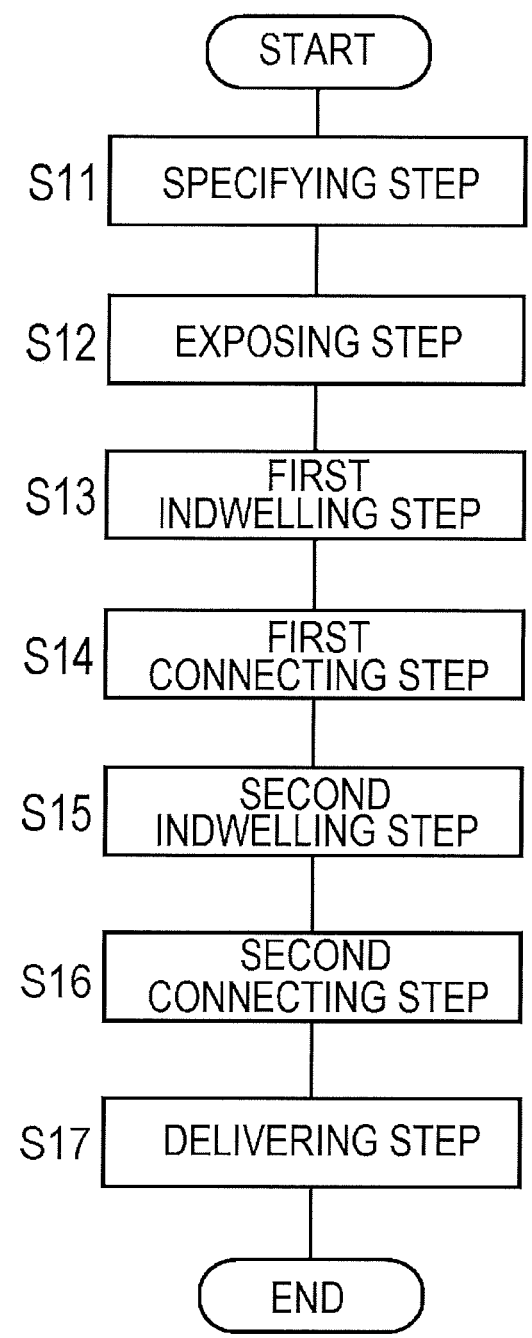
FIG. 4 is a diagram illustrating a sequence of a procedure using the medical device according to the first embodiment.

FIG. 4 is a diagram illustrating a sequence of a procedure using the medical device 10, FIG. 5 is a diagram illustrating a procedure example for lymphedema, and FIG. 6 is a cross-sectional view schematically illustrating a procedure example using the first indwelling needle 100.

Referring to FIG. 4, a lymphedema treatment method generally includes a specifying step (S11) of specifying the lymphatic vessel L corresponding to a treatment target, an exposing step (S12) of cutting a skin and exposing the lymphatic vessel L, a first indwelling step (S13) of puncturing the lymphatic vessel L by the first indwelling needle 100 and indwelling the first catheter unit 110 therein, a first connecting step (S14) of connecting the first catheter unit 110 to the first end portion 310 of the tube member 300, a second indwelling step (S15) of puncturing the vein P by the second indwelling needle 200 and indwelling the second catheter unit 210 therein, a second connecting step (S16) connecting the second catheter unit 210 to the second end portion 320 of the tube member 300, and a delivering step (S17) of delivering the lymph fluid from the lymphatic vessel L to the vein P by using the pump 400. Hereinafter, each of steps will be described.

First, the specifying step (S11) is performed.

Figure 5A:
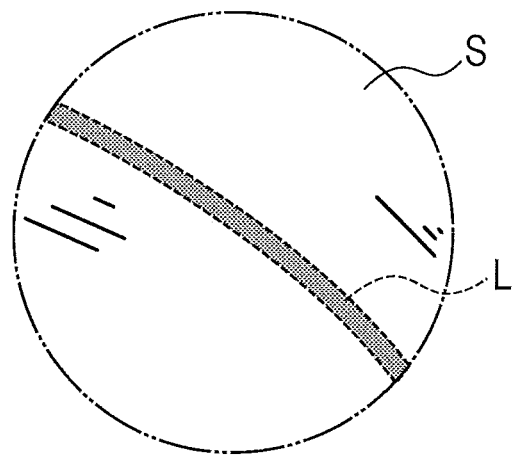
FIGS. 5A and 5B are diagrams illustrating procedure examples for lymphedema.

In the specifying step (S11), the lymphatic vessel L corresponding to a treatment target is specified. As a specifying method, for example, indocyanine green (ICG) fluorescent lymphangiography can be used. FIG. 5A schematically illustrates a state where the lymphatic vessel L is visualized by the ICG fluorescent lymphangiography.

In the ICG fluorescence lymphangiography, ICG contrast agents are injected into several positions of the affected limbs and upper limbs and the flow in the lymphatic vessel L is visualized by using an infrared camera. Then, an arbitrary lymphatic vessel L among the lymphatic vessels L where the flow of the ICG contrast agent stagnates is specified as a treatment target. For example, when treating lymphedema of the lower limbs, the lymphatic vessel L existing in a dorsum, an ankle, a lower leg, a portion above a knee, a portion below a knee, and the like can be selected as a treatment target. When treating lymphedema of the upper limbs, a lymphatic vessel L existing in the periphery of a wrist, a forearm, and an elbow can be selected as a treatment target.

For example, a superficial lymphatic vessel existing right under a skin S can be selected as the lymphatic vessel L. The outer diameter of the selected lymphatic vessel L is preferably, for example, 1 mm or more. In addition, the lymphatic vessel L may be stimulated to expand the outer diameter of the lymphatic vessel L after the exposing process (S12) to be described later.

Next, the exposing step (S12) is performed.

Figure 5B:
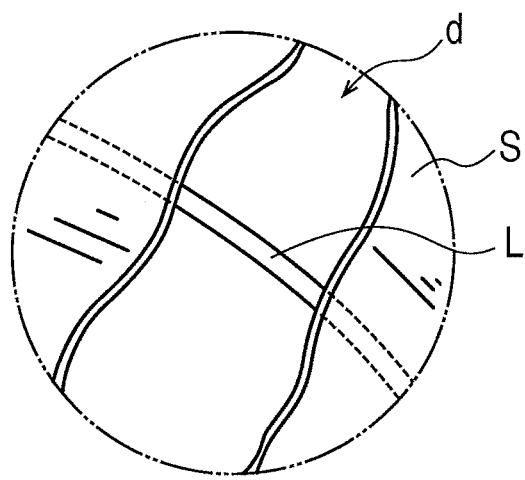

In the exposing step (S12), as illustrated in FIG. 5B, the skin S covering the lymphatic vessel L specified as the treatment target is dissected to form an incision d and the lymphatic vessel L is exposed. The incision can be performed by using a treatment instrument such as a scalpel.

Next, the first indwelling step (S13) is performed.

The first indwelling step (S13) can be performed by using the first indwelling needle 100.

When starting the first indwelling step (S13), the first indwelling needle 100 is prepared in a state where the first catheter unit 110, the inner needle 120, the inner needle hub 130, and the grasping unit 140 are integrally assembled as illustrated in FIG. 2.

Next, as illustrated in FIG. 6A, the inner needle 120 of the first indwelling needle 100 punctures the lymphatic vessel L. When the needle tip 121 of the inner needle 120 penetrates a vessel wall L1 of the lymphatic vessel L, a puncture site (a perforation) t is formed at the vessel wall L1 and the distal end portion of the sheath 111 is inserted through the puncture site t. Then, as illustrated in FIG. 6B, the inner needle 120, the inner needle hub 130, and the grasping unit 140 are removed, and only the first catheter unit 110 is indwelled in the lymphatic vessel L.

Next, the first connecting step (S14) is performed.

In the first connecting step (S14), as illustrated in FIG. 1, the first end portion 310 of the tube member 300 is connected to the catheter hub 112 of the first catheter unit 110. Accordingly, the first catheter unit 110 and the tube member 300 are liquid-tightly connected to each other.

Next, the second indwelling step (S15) is performed.

The second indwelling step (S15) can be performed by using the second indwelling needle 200.

When starting the second indwelling step (S15), the second indwelling needle 200 is prepared in a state where the second catheter unit 210, the inner needle 220, the inner needle hub 230, and the grasping unit 240 are integrally assembled similarly to the first indwelling step (S13).

Next, in the second indwelling step (S15), the inner needle 220 of the second indwelling needle 200 percutaneously punctures the vein P. Then, the inner needle 220, the inner needle hub 230, and the grasping unit 240 are removed and only the second catheter unit 210 is indwelled in the vein P. Additionally, since the second indwelling step (S15) is the same as the first indwelling step (S13), the step will not be illustrated.

Next, the second connecting step (S16) is performed.

In the second connecting step (S16), as illustrated in FIG. 1, the second end portion 320 of the tube member 300 is connected to the catheter hub 212 of the second catheter unit 210. Accordingly, the second catheter unit 210 and the tube member 300 are liquid-tightly connected to each other.

Additionally, the second indwelling step (S15) and the second connecting step (S16) may be performed earlier than the first indwelling step (S13) and the first connecting step (S14). Further, the first connecting step (S14) and the second connecting step (S16) may be performed after the first indwelling step (S13) and the second indwelling step (S15) are performed first.

Next, the delivering step (S17) is performed.

In the delivering step (S17), the pump 400 is operated so that the lymph fluid is delivered from the lymphatic vessel L to the vein P (an arrow direction of FIG. 1) through the tube member 300. As a result, the staying of the lymph fluid causing lymphedema can be eliminated, symptoms such as swelling in the affected area are alleviated, and the treatment of lymphedema is completed.

In the delivering step (S17), the flow rate (the delivery amount) of the lymph fluid delivered by the pump 400 differs depending on the size of the lymphatic vessel L or the vein P, but can be set to, for example, 100 mL/h (milliliters per hour). Further, the delivery time using the pump 400 can be set to, for example, about 1 hour to 24 hours.

After the treatment of the lymphedema, the lymphedema treatment steps (S11 to S17) are periodically repeated. Accordingly, substances causing clogging such as thrombus or impurities such as cholesterol can forcibly flow before the lymphatic vessel L and the vein P are clogged and the lymphedema reoccurs. As a result, a reoccurrence rate after the treatment of the lymphedema can be reduced. The frequency of performing the lymphedema treatment steps (S11 to S17) after the treatment of the lymphedema can be set to, for example, once every three months or once every six months.

Additionally, in the above-described use example, an example has been described in which the lymph fluid is delivered from one lymphatic vessel L to the vein P, but the lymph fluid may be delivered from the lymphatic vessels L to the vein P. In addition, in this case, the same procedure as the above-described use example can be performed. In addition, it can be desirable to change the flow rate of the lymph fluid to be delivered in response to the number of the lymphatic vessels. For example, when the lymph fluid is delivered from two lymphatic vessels L to the vein P, it can be desirable to set the flow rate of the lymph fluid delivered by the pump 400 to be about twice (for example, 200 mL/h) the above-described use example.

As described above, the medical device 10 according to the embodiment can include the tube member 300 that includes the first end portion 310 connected to the lymphatic vessel L (the first body lumen) and the second end portion 320 connected to the vein P (the second body lumen) and the pump 400 (the pressure-feeding unit) that pressure-feeds the lymph fluid (the body fluid) in the lymphatic vessel L to the vein P.

According to the medical device 10 with the above-described configuration, when the lymphatic vessel L and the vein P are connected to each other through the tube member 300 and the lymph fluid in the lymphatic vessel L is pressure-fed to the vein P by the pump 400, the lymph fluid can be forcibly delivered. Further, when the lymph fluid in the lymphatic vessel L is periodically pressure-fed to the vein P by the pump 400, substances causing clogging such as thrombus or impurities such as cholesterol can forcibly flow. As a result, the lymphedema can be treated and a reoccurrence rate after the treatment of the lymphedema can be reduced.

Further, since the pump 400 includes the peristaltic pump mechanism which pressure-feeds the lymph fluid in the lymphatic vessel L to the vein P by peristalizing the tube member 300, it is possible to forcibly deliver the lymph fluid and to adjust the flow rate of the delivered lymph fluid.

In accordance with an exemplary embodiment, the medical device 10 can include the first catheter unit 110 which connects the lymphatic vessel L to the first end portion 310 of the tube member 300 while being indwelled in the lymphatic vessel L and the second catheter unit 210 which connects the vein P to the second end portion 320 of the tube member 300 while being indwelled in the vein P. By using the first catheter unit 110 and the second catheter unit 210, the first end portion 310 and the second end portion 320 of the tube member 300 can be connected relatively easily to the lymphatic vessel L and the vein P.

In accordance with an exemplary embodiment, the medical device 10 can include the first indwelling needle 100 which includes the first catheter unit 110 and the inner needle 120 puncturing the lymphatic vessel L while being disposed in the inner lumen of the first catheter unit 110 and the second indwelling needle 200 which includes the second catheter unit 210 and the inner needle 220 puncturing the vein P while being disposed in the inner lumen of the second catheter unit 210. Accordingly, it is possible to relatively easily perform a procedure of indwelling the first catheter unit 110 in the lymphatic vessel L and a procedure of indwelling the second catheter unit 210 in the vein P.

Second Embodiment

Next, a medical device according to a second embodiment will be described with reference to FIGS. 7 to 11. In addition, since the same reference numerals are given to the same components as those of the above-described first embodiment, a description thereof will be omitted. Further, a point which is not particularly mentioned in the second embodiment can be configured similarly to the above-described first embodiment.

Figure 7:
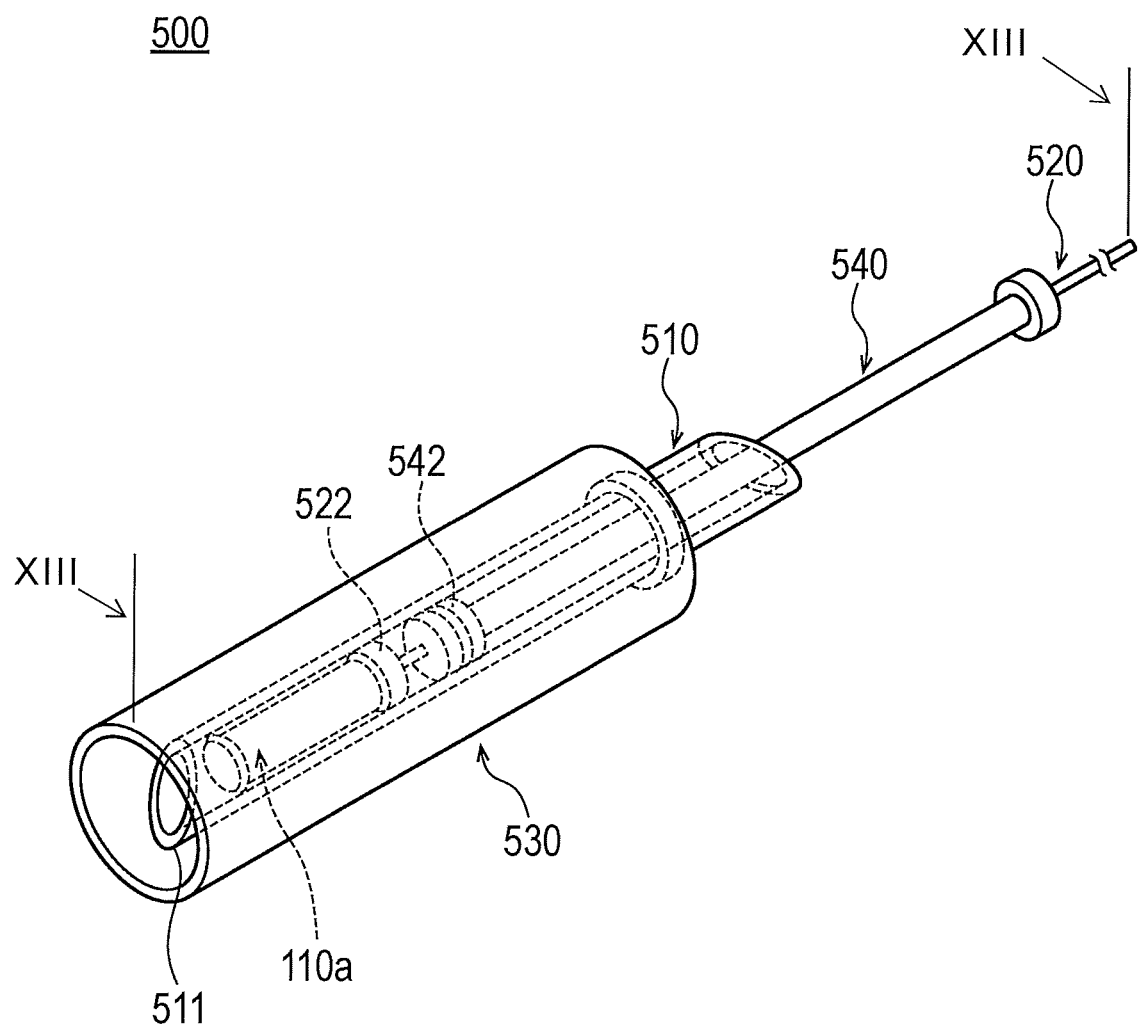
FIG. 7 is a perspective view of a medical instrument according to a second embodiment.
Figure 8:
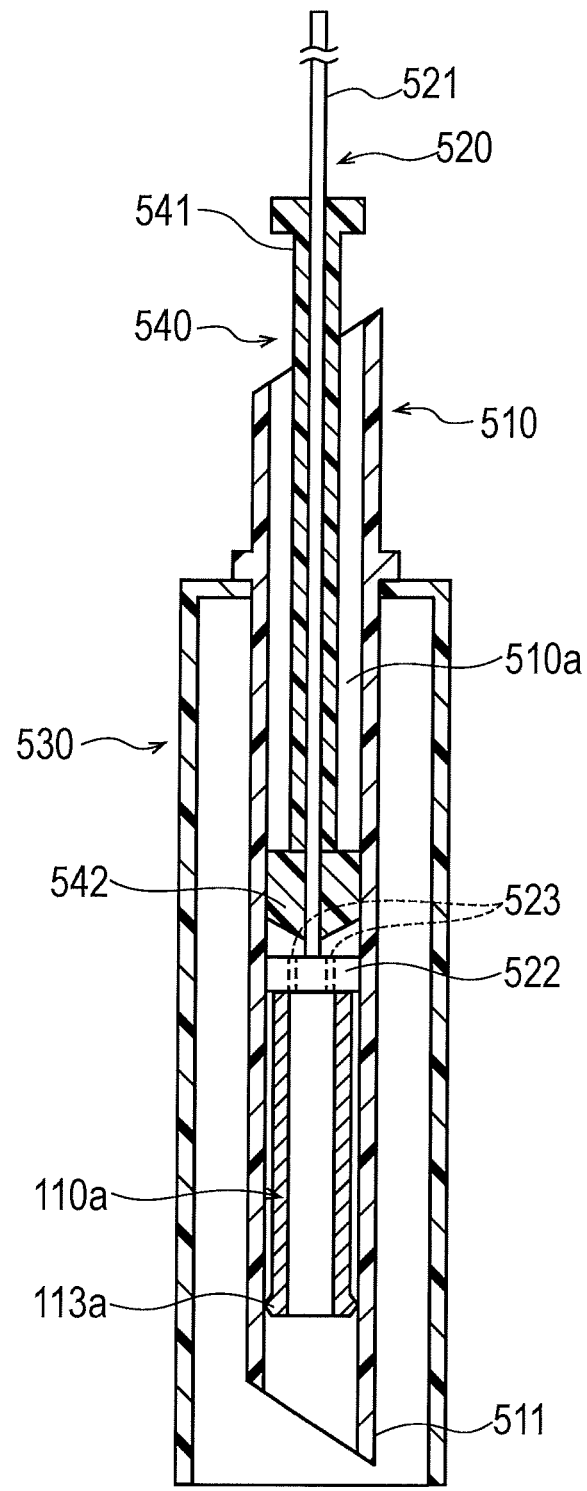
FIG. 8 is a cross-sectional view of the medical instrument according to the second embodiment.

FIG. 7 is a schematic perspective view of a medical instrument 500, FIG. 8 is a cross-sectional view of the medical instrument 500 taken along a line XIII-XIII illustrated in FIG. 7, and FIGS. 9 to 11 are diagrams illustrating procedure examples using the medical instrument 500.

In the above-described first embodiment, the first catheter unit 110 is indwelled in the lymphatic vessel L by using the first indwelling needle 100, but the embodiment has a difference in that a first catheter unit 110a is indwelled in the lymphatic vessel L by using the medical instrument 500. The other configurations are the same as those of the first embodiment.

In accordance with an exemplary embodiment, the medical device according to the second embodiment can include the medical instrument 500 which indwells the first catheter unit 110a in the lymphatic vessel L, the second indwelling needle 200 which includes the second catheter unit 210 punctured into the vein P to be indwelled therein, a tube member 300a which connects the first catheter unit 110a and the second catheter unit 210 to each other, and the pump 400 which pressure-feeds the lymph fluid in the lymphatic vessel L to the vein P through the tube member 300a.

First Catheter Unit 110a

Figure 11A:
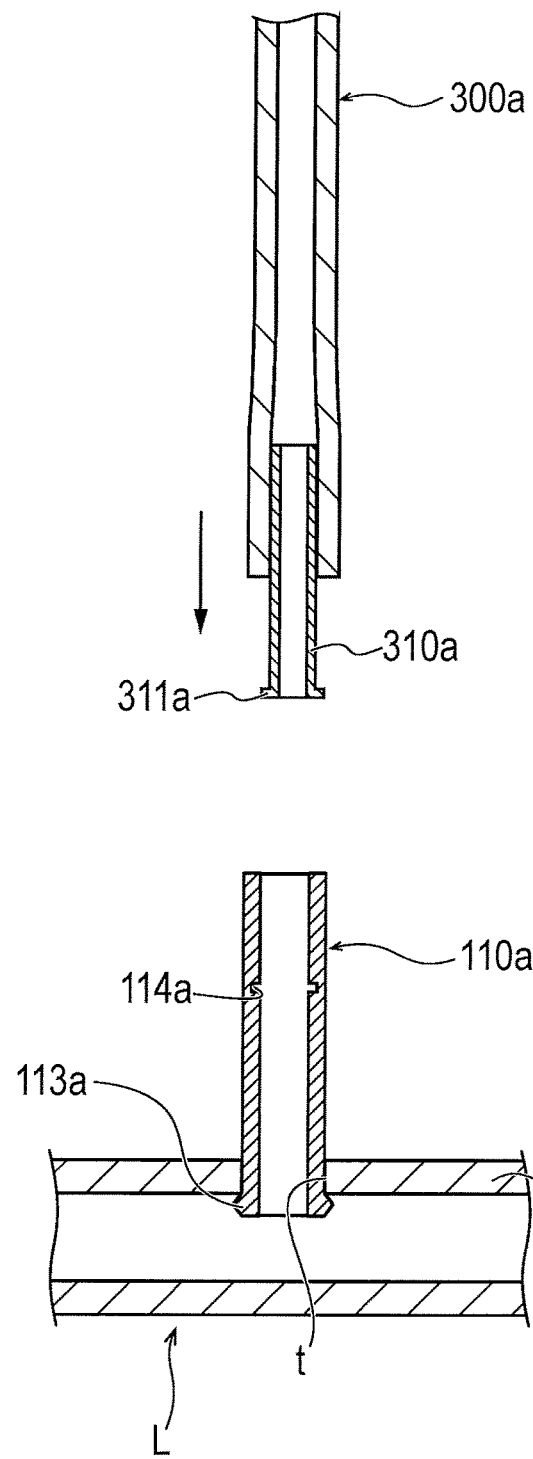
FIGS. 11A and 11B are cross-sectional views schematically illustrating procedure examples using the medical instrument according to the second embodiment.
Figure 11B:
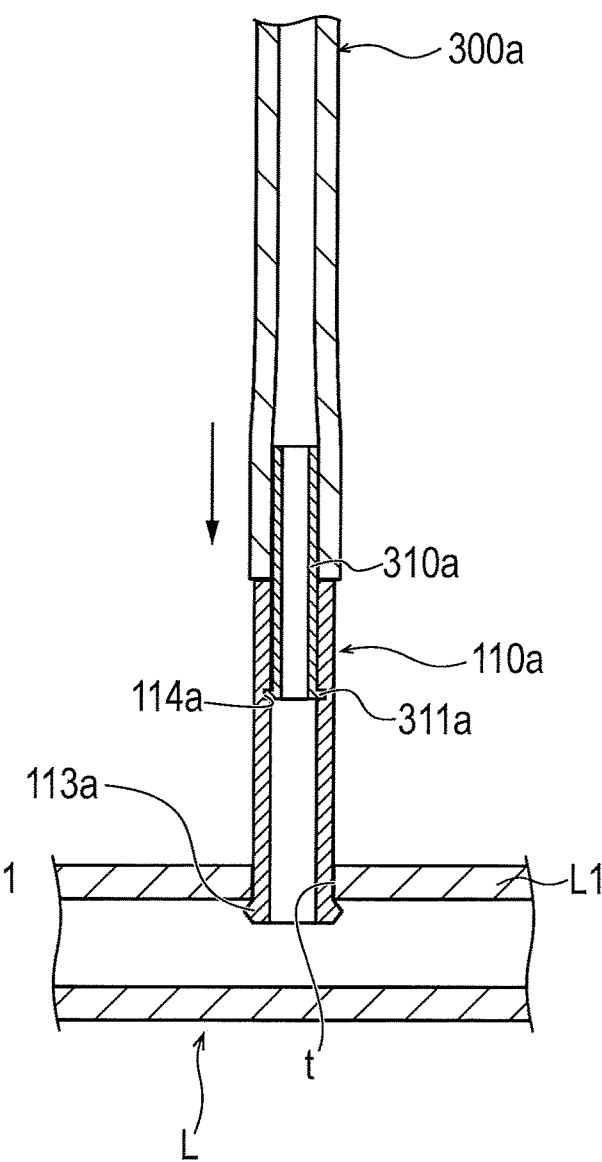

The first catheter unit 110a according to the embodiment is configured as a female connector which can be connected to a first end portion 310a of the tube member 300a corresponding to a male connector as illustrated in FIG. 11B while the first end portion is inserted into the lumen.

In accordance with an exemplary embodiment, a proximal end portion of the first catheter unit 110a is provided with a separation preventing portion 113a which prevents a separation from the puncture site t formed in the lymphatic vessel L. The separation preventing portion 113a can be formed as a convex portion which protrudes outward in the radial direction. As illustrated in FIG. 11A, the separation preventing portion 113a is disposed in the lymphatic vessel L while the first catheter unit 110a is inserted into the puncture site t formed in the lymphatic vessel L.

The separation preventing portion 113a causes the upper surface of the separation preventing portion 113a to contact the inner surface of the vessel wall L1 of the lymphatic vessel L when a separation force (an upward force in FIG. 11A) from the puncture site t is unintentionally applied to the first catheter unit 110a. The separation preventing portion 113a applies a locking force of preventing the separation of the first catheter unit 110a to the lymphatic vessel L by this contact. In this way, when the first catheter unit 110a is provided with the separation preventing portion 113a, it is possible to more stably keep a state where the first catheter unit 110a is fixed to the lymphatic vessel L. Additionally, the shape of the separation preventing portion 113a is not limited to the shape illustrated in the drawings and can be appropriately modified.

As illustrated in FIG. 11A, the first catheter unit 110a includes a concave fitting portion 114a formed at the inner surface thereof. The first end portion 310a of the tube member 300a includes a convex fitting portion 311a which is formed at the outer surface thereof to be fittable to the fitting portion 114a of the first catheter unit 110a. As illustrated in FIG. 11B, when the first end portion 310a is inserted into the first catheter unit 110a so that the fitting portions 114a and 311a are fitted to each other, the connection between the first catheter unit 110a and the tube member 300a can be prevented from being unintentionally released.

Medical Instrument 500

As illustrated in FIGS. 7 and 8, the medical instrument 500 can include a puncture member 510 that includes a lumen capable of accommodating the first catheter unit 110a and includes a needle tip 511 punctured into the lymphatic vessel L, a plunger 520 which operates the movement of the first catheter unit 110a accommodated in the puncture member 510, an outer cylinder 530 which is disposed to cover the outer periphery of the puncture member 510, and a negative pressure generating unit 540 which generates a negative pressure for deforming the vessel wall L1 of the lymphatic vessel L toward the puncture member 510 when puncturing the lymphatic vessel L by the puncture member 510.

Additionally, in the description of the medical instrument 500, a side (the lower side of FIG. 8) in which the needle tip 511 of the puncture member 510 is provided will be referred to as a distal end side and an opposite side (the upper side of FIG. 8) to a side in which the needle tip 511 of the puncture member 510 is provided will be referred to as a proximal end side.

The puncture member 510 is formed as a hollow member. Further, a distal end of the puncture member 510 is provided with the needle tip 511, which can be punctured into the lymphatic vessel L.

The puncture member 510 can be formed of, for example, a resin or metal material having biocompatibility. Further, it is desirable that the puncture member 510 be formed to have a predetermined hardness so that the penetrability of the needle tip 511 is secured to some extent. As the material of forming the puncture member 510, for example, a resin material such as polypropylene, polyethylene, polyethylene terephthalate, polymethyl methacrylate, polycarbonate, polyether ether ketone, polyetherketoneketone, polytetrafluoroethylene, tetrafluoroethylene/perfluoroalkyl vinyl ether copolymer, tetrafluoroethylene/hexafluoropropylene copolymer, tetrafluoroethylene/ethylene copolymer, polyvinylidene fluoride (PVDF), polychlorotrifluoroethylene, chlorotrifluoroethylene/ethylene copolymer, and ultraviolet curing resin, a metal material such as SUS, NiTi, and CoCr, glass, and ceramics can be used. In addition, when the puncture member 510 is formed of a resin material, it is desirable to form the puncture member 510 to be transparent or translucent so that the inside of the puncture member 510 is visible from the outside. Accordingly, it is possible to improve the efficiency of the procedure.

As illustrated in FIG. 8, the plunger 520 can include a bar-shaped body portion 521 and a pushing portion 522 which is disposed at a distal end of the body portion 521 and moves the first catheter unit 110a toward the distal end side. When a user (an operator) who uses the medical device 10 moves the plunger 520 forward by gripping the body portion 521 with fingers, the first catheter unit 110a is moved forward toward the front end side of the puncture member 510 so that the first catheter unit 110a is pushed out from the inner lumen 510a of the puncture member 510.

The negative pressure generating unit 540 is formed as a piston which generates a negative pressure in the inner lumen 510a of the puncture member 510. Specifically, the negative pressure generating unit 540 can include a bar-shaped body portion 541 which is inserted into the inner lumen 510a of the puncture member 510 and a valve body (a plunger) 542 which is provided at a distal end of the body portion 541. The valve body 542 of the negative pressure generating unit 540 is slidably inserted into the inner lumen 510a of the puncture member 510.

Figure 9A:
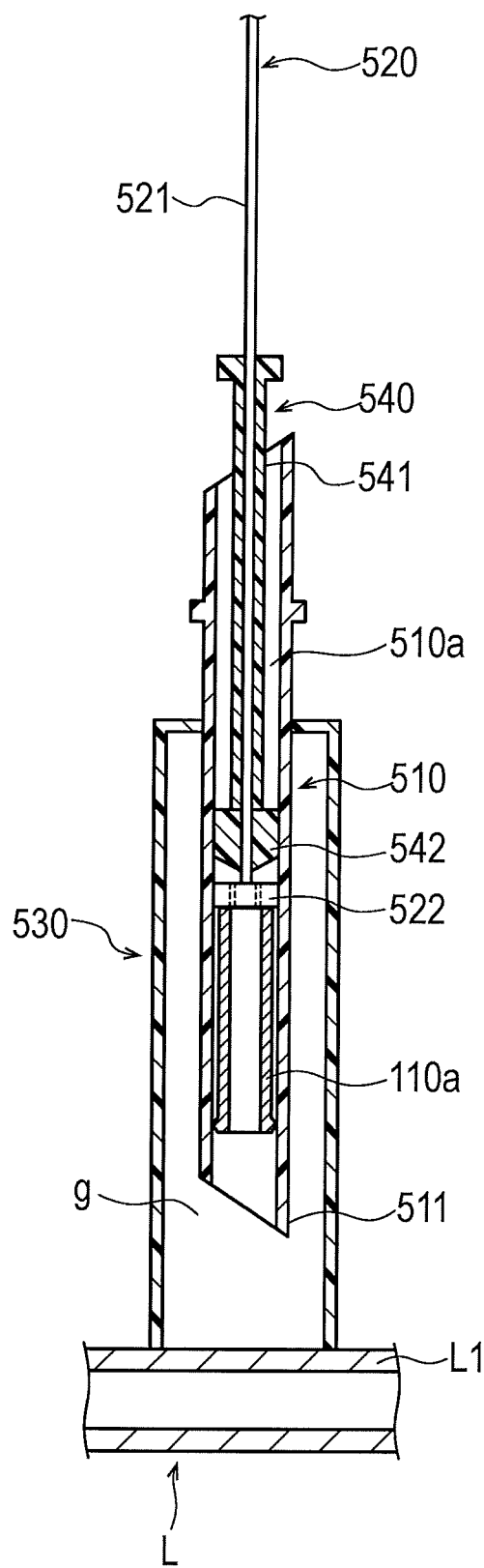
FIGS. 9A and 9B are cross-sectional views schematically illustrating procedure examples using the medical instrument according to the second embodiment.

As illustrated in FIG. 9A, when using the negative pressure generating unit 540, the outer peripheral surface of the puncture member 510 is covered by the outer cylinder 530 and the distal end opening portion of the outer cylinder 530 is disposed to contact the outer surface of the vessel wall L1 of the lymphatic vessel L, thereby forming an air-tight space g in the periphery of the puncture member 510.

Figure 9B:
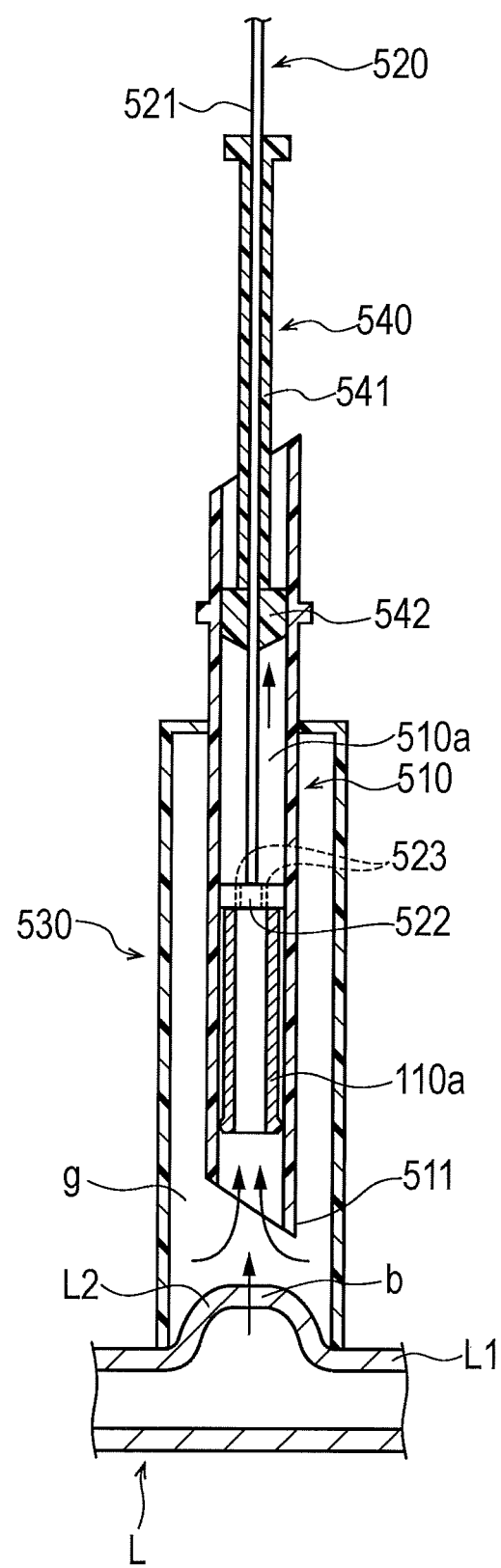

When the valve body 542 of the negative pressure generating unit 540 is slid toward the proximal end side of the puncture member 510 as illustrated in FIG. 9B while the space g is defined by the outer cylinder 530, a suction pressure is applied to the space g through the puncture member 510 and a negative pressure is generated in the space g. Accordingly, the vessel wall L1 of the lymphatic vessel L is lifted and the vessel wall L1 is deformed to approach the needle tip 511 of the puncture member 510. When the vessel wall L1 of the lymphatic vessel L is deformed, the outer diameter of the lymphatic vessel L is expanded at an insertion target position b where the needle tip 511 of the puncture member 510 is inserted in the vessel wall L1. It is possible to appropriately prevent the needle tip 511 of the puncture member 510 from penetrating the lymphatic vessel L when the lymphatic vessel L is punctured by the puncture member 510 in this state.

Further, since the needle tip 511 of the puncture member 510 can be inserted while the insertion target position b is captured by a suction pressure, the collapse of the lymphatic vessel L and the positional deviation with respect to the insertion target position b can be prevented. Further, since the puncturing is performed while the periphery of a bulging portion (a lifted portion) L2 of the vessel wall L1 is covered and protected by the outer cylinder 530, the puncture site t formed by the puncturing can be protected by the outer cylinder 530 immediately after the puncturing. Accordingly, it is possible to keep the puncture site t in a clean state and to prevent the puncture site t or the peripheral portion thereof from being damaged by the influence of the peripheral environment during the procedure.

In addition, as illustrated in FIG. 9B, the pushing portion 522 of the plunger 520 disposed at the distal end side of the valve body 542 is provided with a passage hole 523 formed in the axial direction in a penetrating manner to prevent a disturbance of the suction operation with the sliding of the valve body 542 when a negative pressure is generated in the space g.

In accordance with an exemplary embodiment, it can be desirable that the negative pressure generating unit 540 be formed of an elastically deformable resin material so that the negative pressure generating unit can slide on the inner lumen 510a of the puncture member 510 while keeping the air-tightness with respect to the inner surface of the puncture member 510. As the resin material, for example, natural rubber, butyl rubber, isoprene rubber, butadiene rubber, styrene butadiene rubber, styrene ethylene butylene styrene rubber, ethylene propylene rubber, acrylonitrile butadiene rubber, fluororubber, urethane rubber, polysulfide rubber, chlorinated butyl rubber, silicone rubber, or the like can be used.

Next, an example in use of the medical device according to the embodiment will be described.

In the lymphedema treatment method of the medical device according to the embodiment, the first indwelling step (S13) and the first connecting step (S14) are different from the lymphedema treatment method of the above-described embodiment with reference to FIG. 4. Since the other steps are the same as those in the above-described embodiment, a description thereof will be omitted.

The first indwelling step (S13) can be performed by using the medical instrument 500.

When starting the first indwelling step (S13), the medical instrument 500 is prepared in a state where the first catheter unit 110a, the puncture member 510, the plunger 520, the outer cylinder 530, and the negative pressure generating unit 540 are integrally assembled as illustrated in FIGS. 7 and 8.

Next, as illustrated in FIG. 9A, the space g is formed by the outer cylinder 530 while the distal end portion of the outer cylinder 530 contacts the vessel wall L1 of the lymphatic vessel L.

Next, as illustrated in FIG. 9B, the negative pressure generating unit 540 of the medical instrument 500 is moved to be lifted to the proximal end side to generate a negative pressure in the space g. With this operation, a part of the vessel wall L1 of the lymphatic vessel L is deformed toward the puncture member 510 so that a bulging portion L2 is formed at the vessel wall L1 of the lymphatic vessel L.

Next, as illustrated in FIG. 10A, the puncture member 510 is moved to the distal end side so that the needle tip 511 is punctured into the bulging portion L2 of the lymphatic vessel L. When the needle tip 511 penetrates the vessel wall L1, the puncture site (the perforation) t is formed at the vessel wall L1.

Next, as illustrated in FIG. 10B, the plunger 520 is moved to the distal end side so that the first catheter unit 110a is pushed to the distal end side. By this operation, the first catheter unit 110a is moved to the inside of the puncture site t. At this time, the separation preventing portion 113a of the first catheter unit 110a is disposed at the inside of the lymphatic vessel L. Then, the plunger 520 is moved to the distal end side while the puncture member 510 is moved to the proximal end side so that the first catheter unit 110a is discharged from the puncture member 510. As illustrated in FIG. 11A, the first catheter unit 110a is indwelled in the lymphatic vessel L while the distal end portion is inserted into the lumen of the lymphatic vessel L and the proximal end portion is exposed from the lumen of the lymphatic vessel L.

Next, the first connecting step (S14) is performed.

In the first connecting step (S14), as illustrated in FIG. 11B, the first end portion 310a is connected to the first catheter unit 110a. Accordingly, the first catheter unit 110a and the tube member 300a are liquid-tightly connected to each other.

The same effect as the above-described first embodiment is exhibited also in the medical device including the medical instrument 500 according to the second embodiment.

Further, the medical device includes the puncture member 510 that can be punctured into the lymphatic vessel L and the negative pressure generating unit 540 which generates a negative pressure for deforming the vessel wall L1 of the lymphatic vessel L toward the puncture member 510 when puncturing the lymphatic vessel L by the puncture member 510. When the vessel wall L1 of the lymphatic vessel L is deformed toward the puncture member 510 by the negative pressure generating unit 540, the collapse of the lymphatic vessel L is prevented. For this reason, the puncture member 510 can be punctured into the lymphatic vessel L relatively easily. Further, when the puncture member 510 is punctured into the vessel wall L1 of the lymphatic vessel L while the vessel wall L1 of the lymphatic vessel L is deformed toward the puncture member 510, it is possible to prevent the puncture member 510 from penetrating the lymphatic vessel L.

Further, since the first catheter unit 110a includes the separation preventing portion 113a which helps prevent a separation from the lymphatic vessel L while being indwelled in the lymphatic vessel L, it is possible to stably keep a state where the first catheter unit 110a is indwelled in the lymphatic vessel L.

Although the medical device according to the invention has been described through the embodiments, the invention is not limited to only the configuration described in the embodiment, but can be appropriately modified based on the description of the claims.

For example, the pressure-feeding unit is not limited to a configuration including the peristaltic pump mechanism as long as the body fluid can be pressure-fed and a known pressure-feeding device can be used.

Further, when the body fluid (the lymph fluid) is delivered from the first body lumens (the lymphatic vessels) to the second body lumen (the vein), the tube member may have a configuration in which the body fluid passage is divided and the divided end portions are provided with the first end portions. In this case, the medical device may include any one of the first indwelling needles or the medical instruments for indwelling the first catheter unit in the first body lumens or may include both the first indwelling needle and the medical instrument.

Further, the negative pressure generating unit according to the second embodiment is formed as a piston, but the invention is not limited thereto as long as a negative pressure for deforming the vessel wall of the first body lumen can be generated at the puncture member side. For example, the negative pressure generating unit may be a pump.

Further, the structure of each part of the medical device and the arrangement of the members mentioned in the above-described embodiment can be appropriately changed. Then, the use of additional members can be omitted or other additional members can be appropriately used.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
   a tubular member that includes a first end portion configured to be connected to a first body lumen and a second end portion configured to be connected to a second body lumen;
   a pressure-feeding unit configured to pressure-feed a body fluid in the first body lumen to the second body lumen;
   a first catheter unit configured to connect the first body lumen to the first end portion of the tubular member while being indwelled in the first body lumen;
   a movable puncture member having a lumen configured to accommodate the first catheter unit, the puncture member including a needle tip configured to puncture the first body lumen;
   a second catheter unit configured to connect the second body lumen to the second end portion of the tubular member while being indwelled in the second body lumen;
   an indwelling needle that includes the second catheter unit and an inner needle configured to puncture the second body lumen while being disposed in an inner lumen of the second catheter unit;
   an outer cylinder, the outer cylinder configured to surround an outer periphery of the puncture member and form an air-tight space in the outer periphery of the puncture member, and wherein the puncture member is configured to move relative to the outer cylinder; and
   a negative pressure generating unit configured to generate a negative pressure for deforming a vessel wall of the first body lumen to move the vessel wall toward the puncture member when puncturing the first body lumen with the needle tip of the puncture member.

2. The medical device according to claim 1, wherein the pressure-feeding unit includes a peristaltic pump mechanism configured to pressure-feed the body fluid in the first body lumen to the second body lumen by peristalizing the tubular member.

3. The medical device according to claim 1, wherein the first catheter unit includes a separation preventing portion configured to prevent a separation of the first catheter unit from the first body lumen when indwelled in the first body lumen.

4. The medical device according to claim 1, wherein the first body lumen is a superficial lymphatic vessel and the second body lumen is a vein.

5. A medical device comprising:
   a tubular member that includes a first end portion configured to be connected to a superficial lymphatic vessel and a second end portion configured to be connected to a vein;
   a pressure-feeding unit configured to pressure-feed a body fluid in the lymphatic vessel to the vein;
   a first catheter unit configured to connect the lymphatic vessel to the first end portion of the tubular member while being indwelled in the lymphatic vessel;
   a second catheter unit configured to connect the vein to the second end portion of the tubular member while being indwelled in the vein;
   a movable puncture member having a lumen configured to accommodate the first catheter unit and includes a needle tip configured to puncture the lymphatic vessel;
   a plunger configured to operate a movement of the first catheter unit accommodated in the puncture member into the lymphatic vessel;
   an outer cylinder, the outer cylinder configured to surround an outer periphery of the puncture member and form an air-tight space in the outer periphery of the puncture member, the puncture member configured to move relative to the outer cylinder; and
   a negative pressure generating unit, configured to generate a negative pressure for deforming a vessel wall of the lymphatic vessel toward the puncture member when puncturing the lymphatic vessel with the puncture member.

6. The medical device according to claim 5, wherein the plunger includes a bar-shaped body portion and a pushing portion which is disposed at a distal end of the bar-shaped body portion and configured to move the first catheter unit toward a distal end side of the lymphatic vessel.

7. The medical device according to claim 5, wherein the pressure-feeding unit includes a peristaltic pump mechanism configured to pressure feed the body fluid in the lymphatic vessel to the vein by peristalizing the tubular member.

8. The medical device according to claim 5, wherein the first catheter unit includes a separation preventing portion configured to prevent a separation from the lymphatic vessel while being indwelled in the lymphatic vessel.

9. A method for treating lymphedema with the medical device according to claim 1, the first body lumen being a superficial lymphatic vessel and the second body lumen being a vein, the method comprising:
  indwelling the first catheter connected to one end of the tubular member in the superficial lymphatic vessel and indwelling the second catheter connected to the other end of the tubular member in the vein; and
  pressure-feeding a body fluid in the lymphatic vessel to the vein through the tubular member.

10. The method according to claim 9, further comprising:
  pressure-feeding the body fluid in the lymphatic vessel to the vein by peristalizing the tubular member with a peristaltic pump mechanism.

11. The method according to claim 9, further comprising:
  connecting the lymphatic vessel to the first end portion of the tubular member with the first catheter unit while being indwelled in the lymphatic vessel; and
  connecting the vein to the second end portion of the tubular member with the second catheter unit while being indwelled in the vein.

12. The method according to claim 11, further comprising:
  puncturing the lymphatic vessel with the puncture member and generating the negative pressure for deforming the vessel wall of the lymphatic vessel to move the vessel wall toward the puncture member when puncturing the lymphatic vessel by the puncture member with the negative pressure generating unit.

13. The method according to claim 11, further comprising:
  preventing a separation from the lymphatic vessel while being indwelled in the lymphatic vessel with a separation preventing portion of the first catheter unit.

14. The method according to claim 9,
  wherein the superficial lymphatic vessel is two or more superficial lymphatic vessels.

15. The medical device according to claim 3, wherein the separation preventing portion is a convex portion protruding outward in a radial direction from a proximal end portion of the first catheter unit.

16. The medical device according to claim 1, wherein the outer cylinder has a cylindrical shape extending from one end of the outer cylinder to an other end of the outer cylinder.

17. The medical device according to claim 8, wherein the separation preventing portion is a convex portion protruding outward in a radial direction from a proximal end portion of the first catheter unit.

18. The medical device according to claim 5, wherein the outer cylinder has a cylindrical shape extending from one end of the outer cylinder to an other end of the outer cylinder.

* * * * *